United States Patent [19]

Bisagni et al.

[11] Patent Number: 4,464,354

[45] Date of Patent: Aug. 7, 1984

[54] (3,4-C)-PYRIDO PSORALENS, PROCESS OF PREPARATION, APPLICATION IN COSMETOLOGY AND THERAPEUTICS, AND COSMETOLOGICAL AND PHARMACEUTICAL COMPOSITION WITH THEM

[75] Inventors: Emile Bisagni, Orsay; Louis Dubertret, Paris; Jacqueline Moron, Gif sur Yvette; Dietrich Averbeck, L'Hay les Roses; Dora Papadopoulo, Buc; Jocelyne Blais, Fontenay aux Roses; Paul Vigny, Paris; Maria N. Schwencke, Gif sur Yvette; Ethel Moustacchi, Palaiseau; Silvano Nocentini, Paris; François Zajdela, Antony, all of France

[73] Assignee: Institut National de la Sante et de la Recherche Medicale, Paris, France

[21] Appl. No.: 469,455

[22] Filed: Feb. 24, 1983

[30] Foreign Application Priority Data

Feb. 25, 1982 [FR] France ................................. 82 03157

[51] Int. Cl.³ ................... C07D 491/22; A61K 31/44
[52] U.S. Cl. ..................................... 424/59; 424/256; 546/65; 546/221; 549/470
[58] Field of Search ...................... 546/65; 424/256, 59

[56] References Cited

U.S. PATENT DOCUMENTS 4,260,630 7/1981 Bisagni et al. ...................... 424/283

OTHER PUBLICATIONS

Anderson, Ann. Rev. Pharmacol. Toxicol., (1980), 20, pp. 235–257.

Hönigsmann, "Photochemotherapy with Furocommarins (Psoralens)", Dept. of Dermatology, University of Innsbruck, Anichstr. 35, A-6020 Innsbruck, Austria, pp. 309–320.

Primary Examiner—Donald G. Daus
Assistant Examiner—William A. Teoli, Jr.
Attorney, Agent, or Firm—Oblon, Fisher, Spivak, McClelland & Maier

[57] ABSTRACT

Monofunctional psoralen derivatives having the general formula

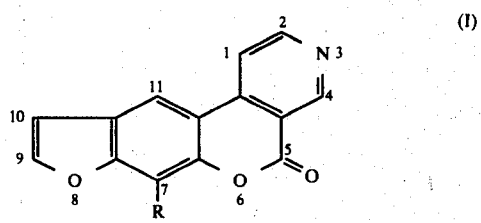

wherein R represents a hydrogen atom, a lower alkyl group having from 1 to 4 atoms, preferably a methyl radical, or a lower alkoxy radical having from 1 to 4 carbon atoms, preferably a methoxy radical are described. The derivatives are photobiologically active and are useful in photochemical therapy and in cosmetics.

16 Claims, No Drawings

(3,4-C)-PYRIDO PSORALENS, PROCESS OF PREPARATION, APPLICATION IN COSMETOLOGY AND THERAPEUTICS, AND COSMETOLOGICAL AND PHARMACEUTICAL COMPOSITION WITH THEM

BACKGROUND OF THE INVENTION

The present invention relates to novel derivatives of psoralen. It concerns more particularly monofunctional derivatives of psoralen consisting of pyrido (3,4-c)-psoralens. The invention also relates to the obtention of such compounds. The invention is also concerned with the use of such compounds in cosmetology, namely for stimulating pigmentation of the skin and as pharmaceuticals, in particular, for the treatment of skin diseases. The invention also relates to cosmetic and pharmaceutical compositions containing such compounds as their active ingredient.

Photochemical therapy which relies on the activation of photoactive molecules of the furocouramin family, namely psoralens, on human skin by ultraviolet A radiations is rapidly developing in dermatology. It is indeed a particularly effective and convenient therapeutic technique for the treatment of benign, chronic dermatoses such as psoriasis which affects 2-3% of the population of the world, and for the treatment of malignant dermatoses such as mycosis fungoides, malignant cutaneous lymphoma, which is rare but has a particularly severe development. This therapeutic treatment has also been employed with a certain amount of success in the treatment of numerous chronic inflammatory skin diseases such a atypical eczema, lichen planus, parapsoriasis guttata, pruritis of the hemodialysed beings and in photodermatoses and depigmentation diseases such as vitiligo.

The preparation of certain psoralen derivatives and the use thereof for the treatment of skin afflictions, particularly psoriasis, has already been proposed. A reference illustrating the prior art in this field is French patent publication No. 2,405;067 for pharmaceutical compositions containing monofunctional derivatives of psoralen for the treatment of skin afflictions. This patent publication, to which reference may be had if necessary, sets out in a detailed manner knowledge at that time relative to derivatives of psoralen and their use as pharmaceuticals.

Briefly, psoralens are used in association with ultraviolet light in phototherapy for skin diseases such as psoriasis. This treatment is known as PUVA therapy. Recent studies have, however, shown that certain bifunctional psoralens such as 8-methoxypsoralen, known by its abbreviation 8-MOP and 5-methoxypsoralen, abbreviation 5-MOP, are carcinogenic in mice after exposure to light in the near ultraviolet range around 365 nm. On the contrary, 3-carbethoxypsoralen which is a monofunctional derivative of psoralen is completely safe from this point of view, while having a therapeutic activity in respect to patients having psoriasis.

The psoralens currently used in therapy such as 8-methoxypsoralen or 5-methoxypsoralen are agents capable of forming cross-links in the DNA, which cross-links are difficult to repair and capable of introducing errors in genetic replication. This property doubtless explains their high mutagenic activity and carcinogenesis in animals. They are therefore effective medicines but propably not devoid of risk for continual use on human beings. This is why photochemical therapy is prohibited for youths up to the age of 18-20 years and one tries to use it as little as possible before the age of 50.

In cosmetology, products are also known which stimulate pigmentation and are comprised of a derivatives of psoralen such as 5-methoxy psoralen (or 5-MOP). They find applications in cosmetic compositions for tanning skin and/or protection of skin against the sun. The drawback with such products is that they are mutagenic.

Summary of the Invention

The invention provides novel monofunctional derivatives of psoralen. These compounds are used as pharmaceuticals namely in the field of treatment of skin diseases and more specially for the treatment of benign or malignant inflammatory dermatoses, viz., psoriasis, mycosis fungoides, constitutional and contact dermatitis, plaque parapsoriasis, parapsoriasis guttata, alopecias, prurigos, lichens planus, pigmentary urticarias as well as pigmentation disorders and photodermatoses.

The compounds according to the invention which have the capacity of stimulating pigmentation of the skin are also useful in the field of cosmetics.

The novel compounds of the invention are pyrido-(3,4-c)-psoralen or pyrido (3,4-c)-furo (3,2-g) coumarins having the general formula I

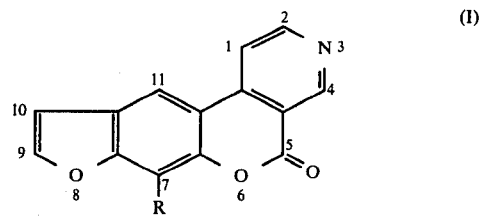

wherein R represents a hydrogen atom, a lower alkyl group having from 1 to 4 carbon atoms, preferably a methyl radical, or a lower alkoxy group having from 1 to 4 carbon atoms, preferably a methoxy radical.

To prepare the compounds of formula I, a hydroxy-6 or hydroxy-6-alkyl-7 (or alkoxy-7) dihydro-2,3 benzofurane acetate is reacted with carboxy-3 piperidone-4 which yields a hexahydro-1,2,3,4,9,10 pyrido (3,4-c) furo (3,2-g) coumarin which may be substituted in position 3 and 7, and subjecting the latter to an aromatization reaction during which both dehydrogenation and removal of the substituent in position 3 are carried out.

The process according to the invention will be more illustrated in the description which follows.

By way of a starting product a compound having the following formula II may be used.

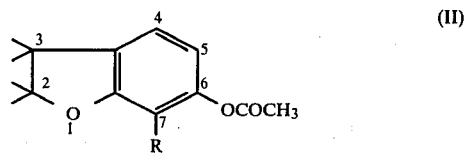

wherein R has the same meaning as above. Such a compound may be obtained in conformity with the process described by E. C. Horning et al in J. Am. Chem. Soc. 70; 3619 (1948) entitled "Furocoumarins. Synthesis of 2,3-dihydropsoralen". In summary, this process comprises the steps of reacting resorcin, optionally alkyl- or alkoxy-substituted in position 2, with chloroacetonitrile in the presence of hydrochloric acid and zinc chloride, treating the resulting product with sodium or potassium acetate which produces a hydroxybenzofuranon, which is then acetylated with acetic anhydride then reduced catalytically, for example, in the presence of a palladium-carbon catalyst, to yield respectively hydroxy-6 or hydroxy-6-alkyl-7 (or alkoxy-7) dihydro-2,3 benzofuran of formula II. The other starting product is a carbethoxy-3 piperidone-4 which is commercially available. In the process according the invention use can be made of the carbethoxy-3 piperidone-4 itself or a derivative substituted in position 1 for example by a methyl group, or preferably, benzyl-1-carbethoxy-3 piperidone-4 of formula III

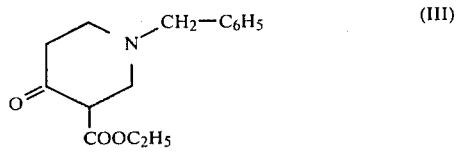

The first step of the process according to the invention comprises reacting the compound of formula II with the carbethoxy-3 piperidone-4, in particular the one represented by formula III. This reaction is known to those skilled in the art as the N. Pechmann synthesis (Organic Reactions, VII, page 1).

This coumarin synthesis comprises condensing a beta-keto ester on a phenol, in particular a polyphenol. The synthesis is carried out in an acid medium. In the case of the present invention acetic acid medium containing hydrogen chloride gas is preferred. The best acid medium comprises acetic acid containing about 6% by weight dry hydrogen chloride gas. The reaction is preferably carried out at normal temperature. There is no reason to increase the temperature, for this generally reduces the yields. The reaction is then continued for several days while stirring. A yield of the order of 75% or more is then obtained. This first step results in hexahydro-1,2,3,4,9,10 pyrido (3,4-c)-furo-(3,2-g) coumarin substituted in position 7 and optionally substituted in position 3, preferably by a benzyl group. In the latter case the intermediate may be represented by formula IV

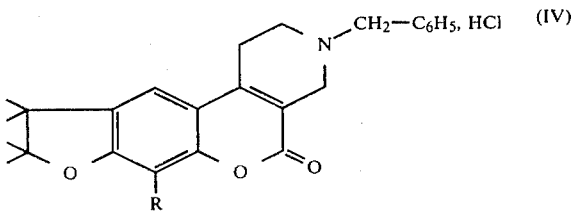

In the foregoing conditions a product in hydrochloride form is obtained directly and it is not necessary to isolate the corresponding base. On the contrary, the process permits the direct treatment of the hydrochloride with improved yield. The second step of the process according to the invention comprises an aromatization reaction in which both dehydrogenation and removal of the substituent in position 3 occur. The reaction is carried out in a solvent in the presence of a highly active dehydrogenation agent, preferably palladium carbon, for example 10% palladium carbon. The solvent must be able to operate under reflux while remaining inert relative to the reagents present. The solvents which have given good results are diphenylether or decahydronaphthalene sold under the trademark Decalin.

The pyrido (3,4-c) psoralens of formula I are thus obtained.

Those skilled in the art will find in Examples 1-4 below details as to the operating procedures for the preparation of the novel derivatives of psoralen of formula I. The compounds of formula I are pharmaceutical useful for the treatment of skin afflictions and disorders and more particularly for the treatment of benign or malignant inflammatory dermatoses, viz., psoriasis, mycosis fungoides constitutional and contact dermatitis, plaque parapsoriasis and parapsoriasis guttata, alopacias, prurigos, lichen planus, pigmentary urticarias as well as pigmentation disorders, and photodermatoses.

These derivatives of formula I possess photobiological properties which are very beneficial in the treatment of skin diseases by PUVA therapy. The treatment of skin disorders with the compounds according to the present invention comprises administering, orally or locally, an effective amount of a compound of formula I and subjecting the patient to light in the near ultraviolet range.

It has been found that at present for local application ointments or solutions containing about 0.1% to about 2% (by weight) of the compound therapeutically effective may be used. Concentrations about 0.5% by weight are preferred.

As excipients for the ointments or solutions according to the invention, excipients may be used which are currently employed which are well known to those skilled in the art. Examples of such excipients are cited by Sch/äefer et al. in Archiv. of Dermatology (1976) which is incorporated by reference.

It is also of course possible to incorporate compounds of the present invention into other compositions, solutions or ointments or add scents, coloring agents, sun filters or preservatives as well as other compounds currently used. It is also possible to combine two or more photosensitizers or photoprotective agents.

To administer orally amounts between 0.5 and 2 mg/kg are preferred.

As mentioned above, the treatment of skin disorders with the compounds according to the invention comprises exposure to near ultraviolet (UVA) radiation in a range essentially comprising wavelengths between 320 and 380 nm. As will be explained below, the dose of radiation at each treatment may at first range from 5 J/cm2 to 10 J/cm2. Nevertheless, doses ranging up to 20 J/cm2 may be used during a short period of time.

The compounds according to the invention may also be used in cosmetics by reason of their property of stimulating the pigmentation of the skin. The invention there encompases cosmetic compositions containing an effective amount of at least one compound according to the invention for producing the pigmentation of the skin in combination with a vehicule suitable for external use. The vehicles of such compositions are well known to those skilled in the art and do not need to be described in greater detail. For the compounds of the invention vehicles similar to those already proposed for cosmetic compositions containing 5-MOP may be used. The cosmetic compositions of the invention may be in cream, lotion, oil, spray form or and in all other products for external use. The compounds of the invention may be associated with sun filters or screens in such compositions. The amount of the active ingredient to be used in the cosmetic compositions of the invention is not critical and may vary according to the intended use thereof. In general, amounts from 0.01 to 0.5% by weight with respect to the composition are suitable.

The novel compounds of the invention have all the following properties:

appreciable photoreactivity with nucleic acids, producing an antiproliferatory effect;

absence of induction of cross-links in DNA;

induction of only mono-additions in DNA, resulting in the stopping of synthesis of DNA and RNA;

slight phototoxic effects, thus causing little or no erythema; and low mutagenic power in contrast to bifunctional furocoumarins currently used in PUVA therapy which involve an appreciable carcinogenic risk.

Example of the preparations of compounds according to the invention will now be given.

EXAMPLE 1

Hexahydro-1,2,3,4,9,10 benzyl-3-pyrido (3,4-c) furo (3,2-g) coumarin (formula IV, R=H)

A mixture of compound II where R=H (2.5 g, 14 mmol) and benzyl-1-carbethoxy-3-piperidone-4 hydrochloride (formula III) (4 g, 13.5 mmol) in solution in 25 ml of icy acetic acid containing 6% of dry hydrogen chloride gas is stirred at ambient temperature for 5 days. The precipitate formed is centrifugally extracted, washed with acetic acid, and dried. 3.78 g (76%) of hydrochloride (formula IV; R=H) mp 234°–236° C. is obtained.

310 mg of this hydrochloride in suspension in 20 ml of water are neutralized by a saturated solution of sodium hydrogen carbonate. After 0.50 hour of stirring the precipitate is centrifugally extracted, washed with water, dried and recrystallized in ethanol to give 206 mg of crystals, mp 163°–165° C.

NMR (CDCl$_3$, δ ppm, 60 MHz) 2.73 (4H, broad s, CH$_2$ in 1 and 2); 3.15 (2H, t, J=8,5 Hz, CH$_2$ in 10); 3.4 (2H, broad s, CH$_2$ in 4); 3.65 (2H, s, CH$_2$–C$_6$H$_5$); 4.56 (2H, t, J=8.5 Hz, CH$_2$ in 9); 6.53 (1H, s, H$_7$); 7.16 (6H, broad s, C$_6$H$_5$—CH$_2$ and H$_{11}$).

Analysis % calculated for C$_{21}$H$_{19}$NO$_3$: C,75.65; H,5.74; N,4.20 Found: C,75.29; H,5.65; N, 4.16.

EXAMPLE 2

Methyl-7-hexahydro-1,2,3,4,9,10 benzyl-3-pyrido (3,4-c) furo (3,2-g) coumarin (formula IV where R=CH$_3$)

This compound is prepared according to the operating procedure described in Example 1 above. Starting with 3.90 g (20 mmol) of the compound (formula II where R=CH$_3$) and 5.9 g (20 mmol) of piperidone (formula III) 5.85 g (15 mmol, 75%) of the hydrochloride (formula IV where R=CH$_3$, mp 260° C.) are obtained.

The liberated base is crystallized in ethanol, mp 208° C.

NMR (CDCl$_3$, δ ppm, 60 MHz) 2.25 (3H, s, CH$_3$ in 7); 2.77 (4H, broad s, CH$_2$ n 1 and 2); 3.23 (2H, t, J=8.5 Hz, CH$_2$ in 10); 3.5 (2H, broad s, CH$_2$ n 4); ,B 3.70 (2H, s, CH$_2$—C$_6$H$_5$); 4.66 (2H, t, J=8.5 Hz, CH$_2$ in 9); 7.16 (1H, s, H$_{11}$); 7.35 (5H, s, C$_6$H$_5$—CH$_2$).

Analysis % calculated for C$_{22}$H$_{21}$NO$_3$: C,76.06;H,6.05;N,4.03 C,75.92;H.6.12;N,4.22.

EXAMPLE 3

Pyrido (3,4-c) furo (3,2-g) coumarin (formula I where R=H) compound 1a 2.33 g (6.31 mmol) of the hydrochloride obtained in Example 1 In suspension in 30 ml of diphenylether are heated under reflux for 5 hours in the presence of 2.1 g of 10% Pd/C (Pd/c: palladium carbon).

The palladium carbon is filtered hot, washed with 5 ml of hot diphenylether. After cooling 500 ml of hexane are added. The resulting precipitate (573 mg) is centrifugally extracted washed with hexane and dried.

After two crystallizations of a methylene chloride/alcohol mixture 375 mg (25%) colorless needless, mp 284°–288° C. were obtained.

The washing of the palladium carbon with methylene chloride and hot alcohol yields another 95 mg of the product.

NMR (CDCl$_3$, δ ppm, 100 Hz) 6.90 (1H, d×d, J=2.3 Hz, J=0.2 Hz, H$_{10}$); 7.54 (1H, d, J=1 Hz; H$_7$); 7.73 (1H, d, J=2.3 Hz, H$_9$); 7.95 (1H, d, J=5.5 Hz, H$_1$); 8.30 (1H, d J=0.4 Hz, H$_{11}$); 8.95 (1H, d, J=5.5 Hz, H$_2$); 9.75 (H, s, H$_4$).

Analysis % calculated for C$_{14}$H$_{17}$NO$_3$: C,70.89;H,2.97;N,5.91 Found: C,70.79;H,3.06;N,5.91.

EXAMPLE 4

Methyl-7-pyrido (3,4-c) furo (3,2-g) coumarin (formula I, R=CH$_3$ compound 1b)

The pyridopsoralen indicated above is prepared as described in Example 3. From 3 g (7.83 mmol) of the hydrochloride prepared in Example 2, there is obtained 928 mg of the product which after two crystallizations of the CH$_2$Cl$_2$/C$_2$H$_5$ OH mixture yields 487 mg (25%) of base, mp 272°–274° C.

NMR (CDCl$_3$, δ ppm, 100 MHz) 2.65 (3H, s, CH$_3$ in 7), 6.87 (1H, d, J=2.2 Hz, H$_{10}$); 7.74 (1H, d, J=2.2 Hz, H$_9$); 7.93 (1H,d,J=5,5 Hz, H$_1$)8.15(1H,S,H$_H$)8.92 (1H, d, J=5.5 Hz H$_2$) 9.56 (1H, s, H$_4$).

Analysis % calculated for C$_{15}$H$_9$NO$_3$: C,71.71;H,3.61;N.5.57 Found: C,71.58;H,3.69;N,5.63.

The novel compounds of the invention have undergone tests in order to evaluate their activity in cosmetics and as pharmaceuticals.

The monofunctional structure of the compounds which constitutes an important property as regards their therapeutic and cosmetic use has been verified by two series of photochemical and photobiological experiments.

Compounds 1a and 1b have similar spectroscopic properties which differ markedly with respect to those of psoralen. The first absorption transition (λ$_{max}$≃330 nm) has notably a higher coefficient of molecular absorption at 365 nm.

Compound 1a free in solution has a good photochemical stability under ultraviolet irradiation up to an incident dose of 27 kJ/m2. Proof of considerable complexation of the compound 1a with the DNA has been obtained by absorption and emission spectroscopy. The solubility of this compound in the DNA is markedly greater than that of the same compound in a mixture of alcohol and water (greater by a factor of at least 10).

Experiments of thermal denaturation-renaturation carried out on the DNA Modified by the compound 1a in the presence of UVA (incident dose ranging up to 27 Kj/m2) yielding values of the non-renaturating fraction of 100%. It is therefore clear that the compound cannot induce biadditions on the DNA.

(1) Use of specifically blocked yeast mutants in the repair of crosslinks of the DNA It is known that photoaddition of bifunctional furocoumarins induces both crosslinks and mono-additions on the bases of DNA. Monofunctional furocoumarins only produce the latter reaction.

For the experiments use was made of a yeast mutant pso2 which has the following properties (a) it is much more sensitive than the wild type from which it derives to the lethal effect of the photoaddition of bifunctional psoralens ("Isolation and characterization of pso mutants sensitive to photo-addition of psoralen derivatives in Saccharomyses cerevisiae", J. A. P. Henriques and E. Moustacchi, Genetics 95, 273–288 (1980) and other crosslinking agents such as bifunctional nitrogenous mustards (Mutagenesis induced by mono and bifunctional alkylating agents in yeast mutants sensitive to photoaddition of furocoumarins (pso), O. Cassier and E. Moustacchi, Mutation Res. 84, 37–47 (1981), or mitomycine C. (b) It is relatively insensitive compared to the wild type to the photoaddition of monofunctional psoralens of the 3-carbethoxypsoralen type or to monofunctional mustards. Similarly pso2 has the same sensitivity as the wild type to ultraviolet radiation at 254 nm or to ionizing radiation which is known to produce essentially lesions of the strands and breaks in the DNA without producing crosslinks in biologically significant doses (c) It has been biologically demonstrated that the pso2 mutant is blocked in the repair of cross-links between strands of the DNA, ("The fate of 8-methoxypsoralen photo-induced cross-links in nuclear and mitochondrial yeast DNA; Comparison of wild type and repair deficient strains, N. Magana-Schwencke", J. A. P. Henriques. R. Chanet and E. Moustacchi, Proc. Natl. Acad. Sci. (1981)). This blocking is specific because the pso2 mutant repair like the wild type, the monoadditions photo-induced on the DNA.

In other words, if the pso2 mutant is shown to be more sensitive than the wild type of the lethal effect of an agent it may be deduced that this agent is capable of producing cross-links of the DNA in such a way that it is a bifunctional compound. On the other hand, if the pso2 mutant has the same sensitivity as the wild type to a given agent, it may be concluded that the agent does not cause cross-links and it is therefore a monofunctional type.

It is found that the pso2 mutant has the same sensitivity as the wild type to the photo-addition of products 1a and 1b. Since the mutant has the same capacity as the wild type to repair the mono-addition lesions, it is clear that the novel products are of the mono functional type. It is also confirmed that the novel products are very photoreactive on the yeast strains.

(2) Direct biochemical verification of the absence of crosslinking in DNA of cells treated with products 1a, 1b and irradiation at 365 nm The validity of the foregoing conclusions is confirmed by in vivo biochemical analysis. Indeed, DNA of cells of the wild type were extracted immediately after treatment with products 1a, 1b at a concentration of $10^{-5}$M and irradiation with two doses of radiation at 365 nm (30% and 5% survival rate). After separating the nuclear DNA and the mitochondrial DNA by gradient density of cesium chloride, the DNA is broken so as to have segments of homogeneous size (one crosslink on the average per molecule for 8-methoxypsoralen), it is denatured and renatured. If the DNA contains cross-links it renatures itself and is found in the double chain form separable by gradient density from single chain DNA. On the other hand, when the DNA does not contain any cross-links it remains in single chain form after renaturation. It was the latter situation which was observed experimentally with products 1a, 1b. The control experiments with 8-methoxpsoralen carried out under the same conditions show cross-linked double strand DNA. For details of the technique used, see: "The fate of 8-methoxypsoralen photo-induced cross-links in nuclear and mitochondrial yeast DNA: Comparison of wild type and repair-deficient strains", N. Magana-Schwencke, J. A. P. Henriques, R. Chanet and E. Moustacchi, Proc. Natl. Acad. Sci. (USA), (1981) and "Absence de pontage interchaines dans l'ADN traité par le 3-carbéthoxypsoralène et une irradiation à 365 nm" (Absence of cross-linking between strands of DNA treated with 3-carbethoxypsoralen and irradiation at 365 nm), N. Magana-Schwecke D. Averbeck, J. A. P. Henriques and E. Moustacchi, C. R. Acad. Sci. Paris 291, 207–210 (1980).

In sum, the use of the pso2 mutant and the direct examination of the DNA of cells treated in vivo clearly show that products 1a, 1b are indeed of the mono functional type.

For the detection of the photo biological activity the unicellular eukaryote system of the Saccharomyces cerevisiae yeast have proved to be very useful. This photobiological activity has in effect been defined by the induction of lethal effects, the induction of "small colony" cytoplasmic mutations (damage in the mitochondrial DNA) and the induction of nuclear mutations (reverse and forward). The experiments were conducted in the customary manner in conformity with the following references:

D. Averbeck, E. Bisagni, E. Moustacchi, Biochim. Biophys. Acta 518, 464 (1978);

D. Averbeck, E. Moustacchi Mutation Res. 88, 133 (1979);

D. Averbeck, E. Moustacchi, Photochem. Photobiol. 31, 475 (1980); and

D. Averbeck, S. Averbeck, F. Dall. Acqua, II Farmaco, 36, 492 (1981).

In the trials on the induction of lethal effects in yeast (i.e., the induction of the inhibition of the capacity of the cells to form a colony) it was observed that in the presence of irradiation at 365 nm (UVA) and with equimolar concentrations ($5 \times 10^{-5}$M) the compound 1a (Example 3) shows an activity close to that of 8-methoxypsoralen (8-MOP) a bifunctional agent widely used in PUVA therapy.

The survival curves prepared for a concentration of $5 \times 10^{-6}$M have shown that the compounds 1a (Example 3) and 1b (Example 4) are respectively 2.5 and 5 times more active on cell survival than 8-MOP. Thus, the dose of UVA must be between 2.5 and 5 times weaker in the case of compounds 1a and 1b than in the case of 8-MOP to attain the same survival rate. At equimolar concentrations ($5 \times 10^{-6}$M) the compound 1b has shown activity close to that of 4,5', 8-trimethylpsoralen (4,5', 8-TMeP) used in photochemical therapy of vitiligo and psoriasis (see M. A. Pathak, J. A. Parrish, T. B. Fitzpatrick, II Farmaco Ed. Sc. 36, 478–491 (1981)). Moreover the solubility of the compounds 1a and 1b in water is similar to that of 4,5', 8-trimethylpsoralen.

It is important to point out that both compounds 1a and 1b do not exert on the yeast photodynamic activity, due to presence of oxygen, on the induction of lethal damages. In this respect they are comparable to furocaumarins such as 8-MOP and 4,5'-dimethylangelicine (4,5'-DMA) but different from 3-carbethoxypsoralen (3-CPs). The photoaffinity of the compounds 1a and 1b for DNA in vivo is respectively about 10 and 20 times greater than that of 8-MOP, therefore makedly much high than that of monofunctional furocoumarin 3-CPs.

If the induction of cytoplasmic mutations is considered as a function of the survivors, the compounds 1a and 1b which are monofunctional derivatives of psoralen, show in 10% of the survivors a rate of induction of cytoplasmic mutation greater than 50%.

The induction of nuclear mutations (reversions and "forward" mutations) has been determined according to procedures described in the above-mentioned articles. In the presence of compounds 1a or 1b at a concentration of $5 \times 10^{-6}M$ the His+ reversions in the haploid strain of Saccharomyces cerevisiae yeast are induced at a rate less than that observed after the treatment with 3-CPs, therefore at a rate very much less than that observed after treatment with the bifunctional agents 8-MOP and 4,5', 8-TMeP for the same survivor rate.

From the analysis of the induction power of forward mutations, i.e., mutation toward the resistance to canavanine, the same conclusion is reached: as a function of UVA doses results are obtained with compounds 1a and 1b ($5 \times 10^{-6}M$) comparable to those obtained with 3-CPs at $5 \times 10^{-5}M$. As a function of the surviving fractions, compounds 1a and 1b are markedly less mutagenic than 3-CPs and the bifunctional compounds 8-MOP and 4,5', 8-TMeP.

The therapeutic effect of the novel furocoumarins was again appreciated from their capacity to inhibit cellular syntheses as Bordin et al already showed in 1972 with other furocoumarins. (F. Bordin, F. Bacchetti and L. Musajo, Experientia 28, 148 (1972)).

In two human fibroblastic strains in culture (GM 1603 and Ja . . . ) the photosensitiver effect of compounds 1a and 1b was measured compared with that of 8-methoxypsoralen (8-MOP) and 3-carbethoxypsoralen (3-CPs) on the synthesis of DNA, RNA and proteins.

The cells cultivated in Petri dishes having a minimum Eagle medium with 10% embryonic calf serum were marked by precursors which were specific to the exponential phase of growth. The rates of synthesis were estimated by measuring the incorporation of the radioactive precursors in the acid-precipitable material (see S. Nocentini, Biochim. Biophys., Acta 521, 160 (1978)).

The results indicate that the photosensitization of human fibroblasts by those various furocoumarins diminish the synthesis of DNA and RNA as a function of the UVA dose (at 365 nm). Compounds 1a and 1b have an inhibition capacity of the same order. They are slightly more powerful than 8-MOP and much more than 3-CPs under the experimental conditions utilized. For all the products the inhibition of the synthesis of RNA is slightly weaker than that of DNA for the same dose of irradiation. The synthesis of the proteins is on the other hand little affected.

In conclusion, the above results indicate that compounds 1a and 1b have a photoaffinity in respect to DNA which is markedly greater than that of 8-MOP and a photoreactivity which is close to that of 4,5'-8-trimethylpsoralen. The results on the induction of "small" cytoplasmic mutations (damage to the mitochondrial DNA) and on the induction of nuclear mutations show that the two compounds photoreact with the DNA in a monofunctional way, i.e., they are incapable of forming cross-links in the DNA.

The above results were confirmed by tests intended to measure on the cell cultures the antiproliferatory effect of the novel compounds according to the invention.

The photobiological activity of the two monofunctional componds 1a and 1b have been studied in mammalian cells in vitro in order to determine their antiproliferatory effect. This effect was compared with that of 8-methoxypsoralen (8-MOP), a bifunctional furocoumarin.

A diploid strain of V79 chinese hamster cells were used.

The action of the compounds on cell survival (i.e. the antiproliferatory effect) was determined by measuring their power to inhibit the capacity of cells to form colonies. The technique used is that described by C. F. Arlett (1977). (C. F. Arlett, "Mutagenicity testing with V79 chinese hamster cells", Handbook of Mutagenicity Test Procedure, edited by B. J. Kilbey, Elsevier/North Holland Biomedical Press, 1977, p. 175-192).

The antiproliferatory effect of the compounds 1a and 1b have been determined for a concentration of $5 \times 10^{-6}M$. The UVA radiation of 265 nm ranged between 200 and 3200 J/cm2. In the absence of radiation no diminution of cell survival for either of the two compounds was observed.

With a view to comparing the antiproliferatory effects of the compounds studies, the living dose $LD_{10}$ which leaves 10% survive was determined. The values of $LD_{10}$ are respectively 540 and 1800 J/cm2 for compounds 1b and 1a. Compound 1b is therefore markedly more effective than compound 1a, both having a considerable photosensitivity.

With regard to the comparison with the bifunctional furocoumarin 8-MOP which is widely used in PUVA therapy, it should be noted that for the same concentration of $5 \times 10^{-6}M$ the $LD_{10}$ is 3800 J/cm2. This enables us to affirm that both the novel compounds 1a and 1b although they are monofunctional have, compared to 8-MOP, a higher antiproliferatory effect.

In comparison with furocoumarins presently used in photochemical (PUVA) therapy, viz., 8-MOP and 4,5', 8-TMeP the antiprofileratory effect of the novel products 1a and 1b is comparable to that of bifunctional furocoumarins while involving lower mutagenic and carcinogenic risks. These novel compounds therefore have a phototherapeutic activity which is of greater interest than that of similar, known compounds.

The clinical and therapeutic activity of compounds 1a and 1b has been also measured on human skin.

10 mg of compounds 1a and 1b were diluted in 2 g of a purified lanolin commercially available under the name ROC hydrocerine which was made liquid by heating to 60° C.

This local preparation was first tested on normal human skin (of the forearm). An amount of 10 micrograms/cm2 of products 1a and 1b was applied to a circular cutaneous surface 3 cm in diameter. The two products were left on the skin for 2 hours to insure a sufficient cutaneous penetration. After this period of 2 hours ultraviolet A irradiation at 5 J/cm2 was applied to the two zones tested and no precocious or delayed erythema was observed with these doses of irradiation. The same experiment was repeated a second time with irradiation of 20 J/cm2 through a glass plate in order to filter out all the ultraviolet B radiation. Under these conditions slight erythema appeared 72 hours after the irritation. This erythema, slightly apparent, continued for 18 days. Pictures were taken on the sixth day but also a reflective photoplethysmographic study was also carried out and permitted a doubling of the systolic pulse of the capillaries at the erythmatic zones to be seen. The erythma and the result of the reflective photoplethysmograph were totally identical for products 1a and 1b. There was no desquamation or local pain during the evolution of these erythmas. These tests demonstrate that products 1a and 1b are very mildly erythmatogenic under conditions where 3-carbethoxypsoralen is not. The erythma only appeared in doses of irradiation where are twice that customarily used in a therapeutic treatment.

Products 1a and 1b have also been tested in the same excipient on a high inflammatory psoriatic plaque. These two products were applied to surfaces having a 3 cm diameter. On a third surface the excipient alone was applied. The doses of products 1a and 1b applied were 30 micrograms/cm2. The products and the lanolin alone were applied 2 hours before irradiation. The doses of irradiation were, at the outset, 5 J/cm2 and the treatment were repeated every two days, more particularly every Monday, Wednesday and Friday morning. From the fourth treatment a slight decrease of the squamae was observed in the zones where products 1a and 1b were applied and a tangible reduction of the infiltration. At that time pictures do not permit such a difference to be recorded. The complete whitening of the zones treated with products 1a and 1b were obtained by the tenth treatment after a total dose of 50 J/cm2. This whitening was practically as fast in the zones treated with products 1a and 1b. The zone treated with lanolin alone remained unchanged. During this course of treatments no erythema or secondary effect was observed in the zones treated with products 1a and 1b, although hyperpigmentation was found in the two zones, in particular the one treated with product 1b.

This therapeutic test comprising the application of 30 μg/cm2 of products 1a and 1b two hours before UVA irradiations was carried out on three patients. In two cases product 1b was found to be moderately better than product 1a and in particular more pigmentogenic. In the third case only product 1b produced the complete whitening of the psoriasis, product 1a did not have a detectable antipsoriatic action. It therefore seems that product 1b has an antipsoriatic action superior to that of product 1a after a particularly short course of 10 treatments of PUVA, that is a total dose of 50 J/cm2.

A second therapeutic test intended to compare the antipsoriatic effectiveness of 8-methoxypsoralen and product 1b was conducted on three patients. The concentrations of 8-MOP and product 1b were $10^{-2}$M in the same excipient as that used in the previous therapeutic test. Both preparations were applied on two rounded zones 3 cm in diameter, located on the same psoriatic plaque and were irradiated according to the same procedure of gradually increasing ultraviolet irradiation until a maximum of 10 J/cm2 per treatment. For these three patients product 1b was found to be more effective than 8-methoxypsoralen. One patient has no further treatment after the end of the test period, and rapid deterioration in the zone treated with 8-methoxypsoralen was observed whereas the corresponding zone treated with product 1b showed practically no deterioration during this period. This additional therapeutic tests therefore demonstrates that product 1b is more effective than 8-methoxypsoralen and after treatment the deterioration is less rapid with product 1b than with 8-methoxypsoralen.

The pigmentogenic properties of products 1a and 1b have been tested on normal skin at a concentration of 0.5%. Visible pigmentation was observed on three normal patients tested with product 1b in all three cases after total UVA doses of 140 J/cm2. On the other hand, product 1a produced a very slight pigmentation, hardly visible, in only two of the three patients. It seems that the pigmentogenic properties of product 1b are therefore superior to those of product 1a.

In conclusion, compounds 1a and 1b demonstrate good antipsoriatic activity when applied locally. Product 1b has been shown to be more effective than 8-methoxypsoralen used in strictly identical conditions of concentration and irradiation. Compounds 1a and 1b are pigmentogenic and product 1b is more pigmentogenic than product 1a. Finally, products 1a and 1b are not erythmatogenic in conditions of irradiation customarily used in human therapy. Products 1a and 1b are, moreover, less mutagenic than 3-carbethoxypsoralen, as shown above.

The best therapeutic results have been obtained up to now with compound 1b. These novel compounds 1a and 1b may therefore be used effectively in photochemical therapy for all psoriatic patients, even for photochemical therapy on children. This possibility of treating children is of particular interest, for there is at the present time little therapeutic treatment which may indeed be used on them.

By reason of their pigmentogenic effects the novel compounds 1a and 1b may also find uses in cosmetics.

What we claim is:

1. Pyrido (3,4-c)-psoralens or pyrido (3,4-c) furo (3,2-g) coumarins having the following formula:

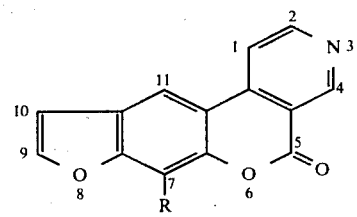

wherein R is selected from the group consisting of a hydrogen atom, and a lower alkyl group having from 1 to 4 carbon atoms.

2. Pyrido (3,4-c)-psoralens or pyrido (3,4-c) furo (3,2-g) coumarins of claim 1, wherein the lower alkyl group is a methyl radical.

3. Pyrido (3,4-c)-psoralens or pyrido (3,4-c) furo (3,2-g) coumarins of claim 1, wherein the radical R is selected from the group consisting of a hydrogen atom and the methyl radical.

4. A pharmaceutical composition to treat inflammatory skin disorders for administering to a subject having said inflammatory skin disorder containing a pharmaceutically effective amount of an active ingredient comprising pyrido (3,4-c)-psoralen or pyrido (3,4-c) furo (3,2-g) coumarin having the following formula:

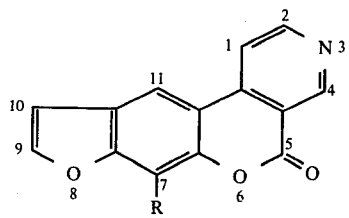

wherein R is selected from the group consisting of a hydrogen atom, and a lower alkyl group having from 1 to 4 carbon atoms and a pharmaceutically acceptable vehicle.

5. The pharmaceutical composition of claim 4, wherein the pharmaceutically acceptable vehicle is suitable for local administration and comprises an ointment or solution.

6. The pharmaceutical composition of claim 4, wherein said pharmaceutically effective amount of the active ingredient is from about 0.1–2% by weight of the pharmaceutical composition.

7. The pharmaceutical composition of claim 6, wherein the pharmaceutically effective amount is about 0.5% by weight of the pharmaceutical composition.

8. The pharmaceutical composition of claim 4 wherein said composition is administered with other agents selected from the group consisting of ointments, solutions, coloring agents, sun filters, preservatives, photosensitizers, photoprotective agents and ultraviolet radiation.

9. The composition of claim 4 wherein said composition has photochemical or photobiological activity.

10. The composition of claim 9 wherein said photochemical or photobiological activity is induced by exposure to ultraviolet light.

11. The composition of claim 4 wherein said composition is pigmentogenic.

12. The composition of claim 4 wherein said pigmentogenicity is induced by exposure to ultraviolet light.

13. The composition of claim 4 wherein said inflammatory skin disorder is pigmentation disorder or photodermatoses.

14. The composition of claim 13 wherein said skin disorder is psoriasis.

15. A cosmetic composition with at least one pyrido (3,4-c)-psoralen or pyrido (3,4-c) furo (3,2-g) coumarin having the following formula:

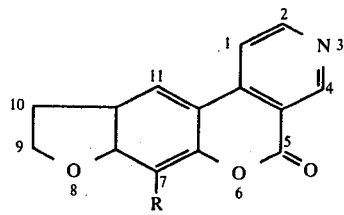

wherein R is selected from the group consisting of a hydrogen atom, and a lower alkyl having from 1 to 4 carbon atoms, and a vehicle suitable for external use.

16. The cosmetic composition of claim 15, wherein the active ingredient is present in an amount from about 0.01 to about 0.5% by weight with respect to the total cosmetic composition.

* * * * *